United States Patent [19]

Black et al.

[11] Patent Number: 4,490,859
[45] Date of Patent: Jan. 1, 1985

[54] ARTIFICIAL HEART VALVES

[75] Inventors: Martin M. Black; Philip J. Drury, both of Sheffield, England

[73] Assignee: University of Sheffield, Sheffield, England

[21] Appl. No.: 459,037

[22] Filed: Jan. 18, 1983

[30] Foreign Application Priority Data

Jan. 20, 1982 [GB] United Kingdom ............ 8201793

[51] Int. Cl.³ .............................................. A61F 1/22
[52] U.S. Cl. ............................................ 3/1.5
[58] Field of Search ............................... 3/1.5, 1

[56] References Cited

U.S. PATENT DOCUMENTS

| 3,739,402 | 6/1973 | Cooley et al. | 3/1.5 |
| 3,755,823 | 9/1973 | Hancock | 3/1.5 |
| 3,983,581 | 10/1976 | Angell et al. | 3/1.5 |
| 4,340,977 | 7/1982 | Brownlee et al. | 3/1.5 |

Primary Examiner—Ronald L. Frinks
Attorney, Agent, or Firm—King, Liles and Schickli

[57] ABSTRACT

A bioprosthetic mitral valve replacement comprises a flexible frame (1) having a ring-shaped base (2) and at least a pair of upstanding posts (3), which divide the base into at least two portions (2A, 2B) of varying flexibility, together with animal tissue leaflets (4) each having a periphery consisting of a free portion (4A) extending between the tips (3X) of posts (3) and a fixed portion (4B) secured and sealed to corresponding sides of the posts and the adjacent portion of the base. A bicuspid mitral valve replacement has a pair of posts (3) disposed at opposite ends of a diameter of the undistorted base (2), or displaced therefrom towards the portion (2A) of lesser flexibility to accommodate leaflets (4) of unequal size. The frame (1) is formed of Delrin covered with Dacron cloth, the Delrin having differing thicknesses to either side of the posts (3) which merge into the base (2) by way of a continuous curve (6) on each side. The leaflets (4) are cut from flat sheet in a special way to avoid stress-fixing.

7 Claims, 12 Drawing Figures

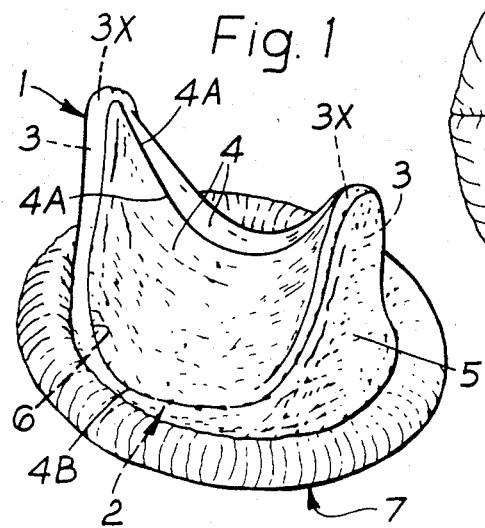
Fig. 1
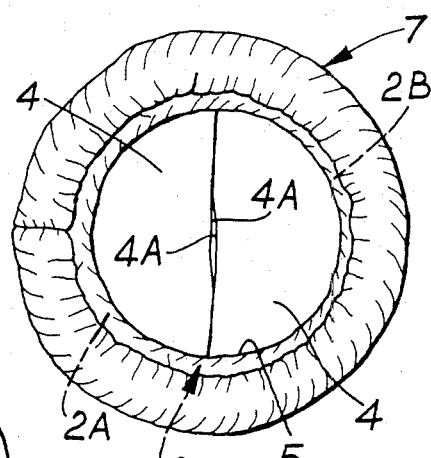
Fig. 2
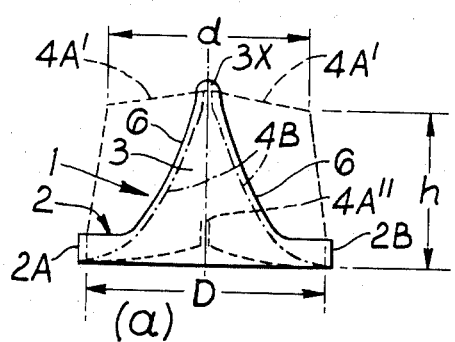
(a)
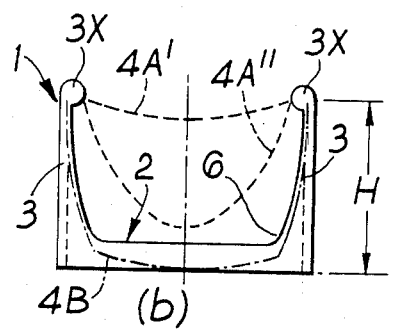
(b)
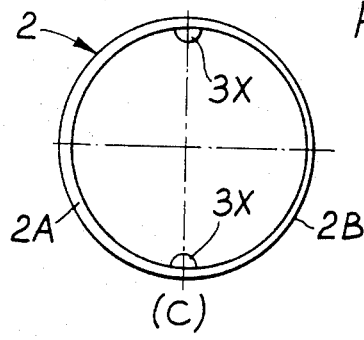
(c)
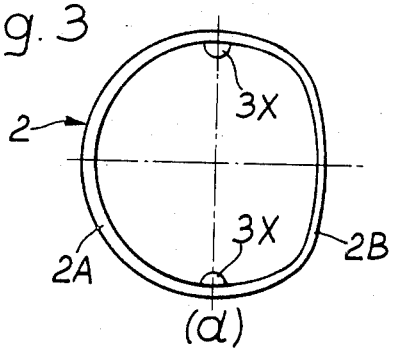
(d)
Fig. 3

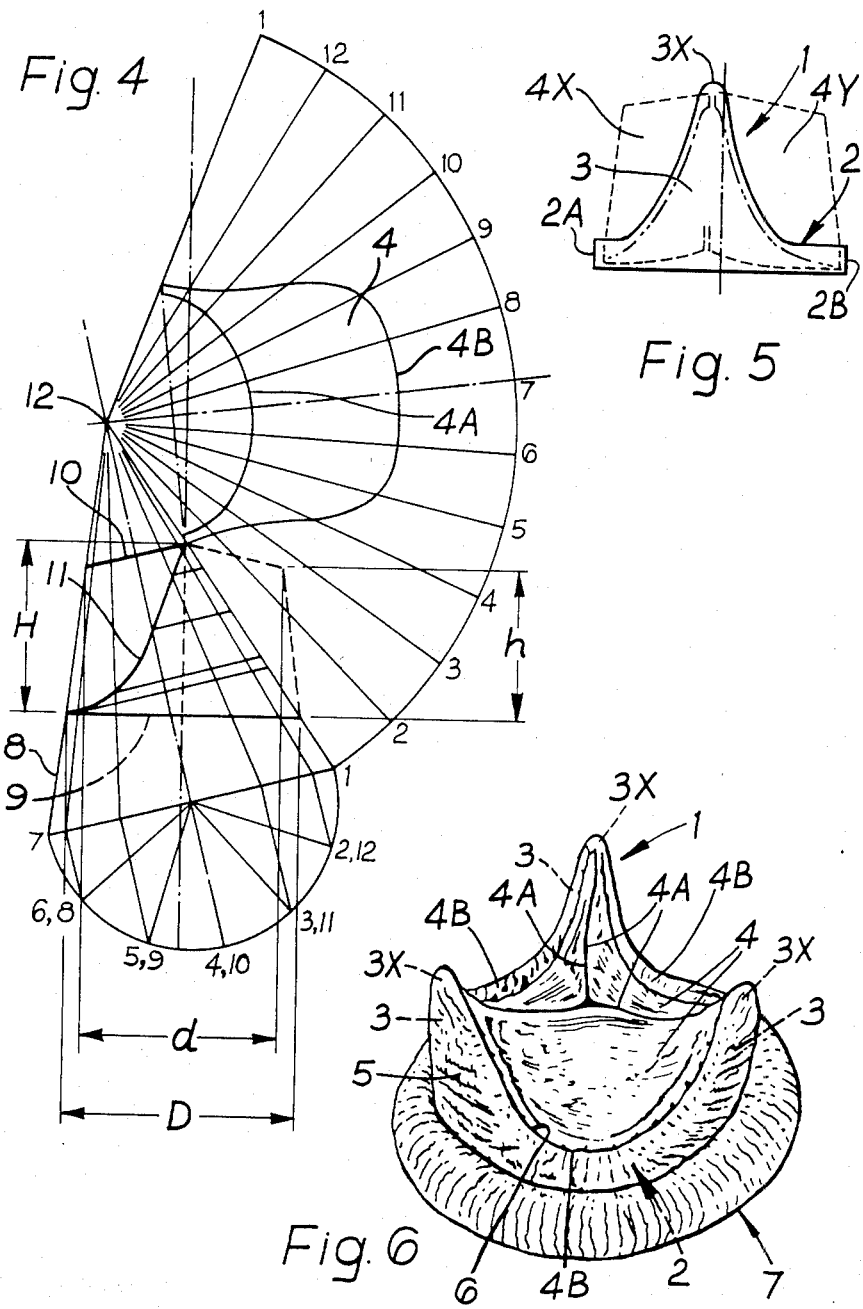

|  | PRIOR ART I IONESCU-SHILEY | | | PRIOR ART II HANCOCK | | | INVENTION FIGURES 1 & 2 | | |
|---|---|---|---|---|---|---|---|---|---|
|  | Pressure Drop (mm Hg) | | Regurgitation cm³/beat | Pressure Drop (mm Hg) | | Regurgitation cm³/beat | Pressure Drop (mm Hg) | | Regurgitation cm³/beat |
|  | Mean | Maximum |  | Mean | Maximum |  | Mean | Maximum |  |
| Mean Flow 180cm³/sec. Stroke Volume 65cm³ | 1.6 | 7.6 | 7.1 | 5.8 | 14.8 | 3.6 | 1.8 | 7.6 | 5.5 |
| Mean Flow 225cm³/sec. Stroke Volume 81cm³ | 2.9 | 10.9 | 6.8 | 8.7 | 21.8 | 4.0 | 3.1 | 10.9 | 5.9 |
| Mean Flow 272cm³/sec. Stroke Volume 98cm³ | 4.3 | 14.8 | 7.1 | 12.0 | 29.6 | 4.7 | 4.4 | 15.4 | 5.7 |

Fig. 9

ARTIFICIAL HEART VALVES

This invention relates to artificial heart valves and has for its object the provision of a bioprosthetic bicuspid or tricuspid mitral valve replacement affording a performance closely comparable to that of a natural mitral valve.

According to the present invention, a bioprosthetic mitral valve replacement comprises a flexible frame having a ring-shaped base and at least a pair of upstanding posts, which divide the base into at least two portions of varying flexibility, together with animal tissue leaflets each having a periphery consisting of a free portion extending between the tips of posts and a fixed portion secured and sealed to corresponding sides of the posts and the adjacent portion of the base.

In use in a heart, the ring-shaped base is attached to the circumference of the auriculo-ventricular orifice (preferably through an intermediate sewing ring) with the portion of the base of greater flexibility adjacent the aortic valve, whereby the base can deform from a substantially circular shape to an approximate D-shape, as is the case with the natural mitral valve.

In a bicuspid mitral valve replacement a pair of posts may be disposed at opposite ends of a diameter of the undistorted base, or they may be displaced therefrom towards the portion of lesser flexibility to accommodate leaflets of unequal size, as in the natural mitral valve. In a tricuspid mitral valve replacement three posts may be disposed at regular intervals round the undistorted base, or at other intervals dictated, for example, by the anatomical requirements of coronary ostia in aortic valve replacements.

The flexible frame is preferably formed of Delrin (Registered Trade Mark) covered with Dacron (Registered Trade Mark) cloth, with the differential flexibility afforded by differing thicknesses of the frame material to either side of the posts. The posts preferably merge at each side into the respective arcuate portions of the ring-shaped base, with the merging preferably being by way of a continuous curve from the rounded tip of one post to the rounded tip of the other post.

The valve leaflets are preferably cut from a flat sheet of fully fixed (i.e. gluteraldehyde treated) animal tissue (e.g. bovine or calf pericardium), but the shape of each leaflet preferably corresponds to a portion of a surface of a cone which portion is defined by the intersections on the conical surface of two parallel flat planes having peripheries on the conical surface corresponding in length respectively to the circumference of the ring-shaped base and the distance between the tips of the posts of the frame, and a third intersection on the conical surface of a curved plane concave towards the apex of the cone and intersecting the two parallel flat planes at opposite sides of the cone, the spacing of the flat planes and the curvature of the curved plane being such that the development of the curved plane on the conical surface matches in length and curvature the continuously blending curve of one arcuate portion of the ring-shaped base and the adjacent sides of the posts, so that no moulding or stress-fixing of the leaflet material is required.

Two embodiments of the invention and a slight modification of one, will now be described, by way of example only, with reference to the accompanying drawings, in which:

FIG. 1 is a perspective view of a bicuspid mitral valve replacement in accordance with the invention;

FIG. 2 is an underneath view or inflow aspect of the valve replacement of FIG. 1;

Figure 7:
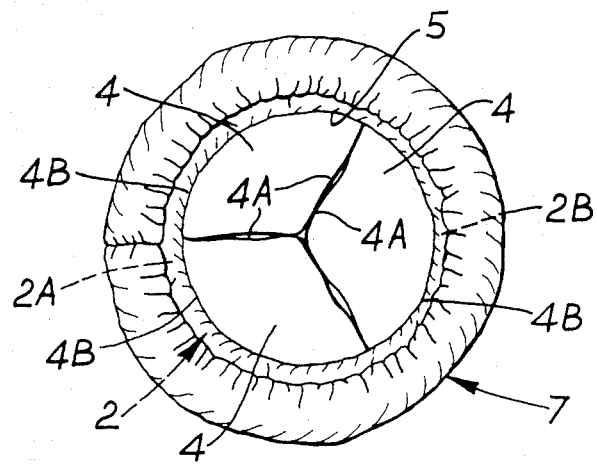
Figure 8:
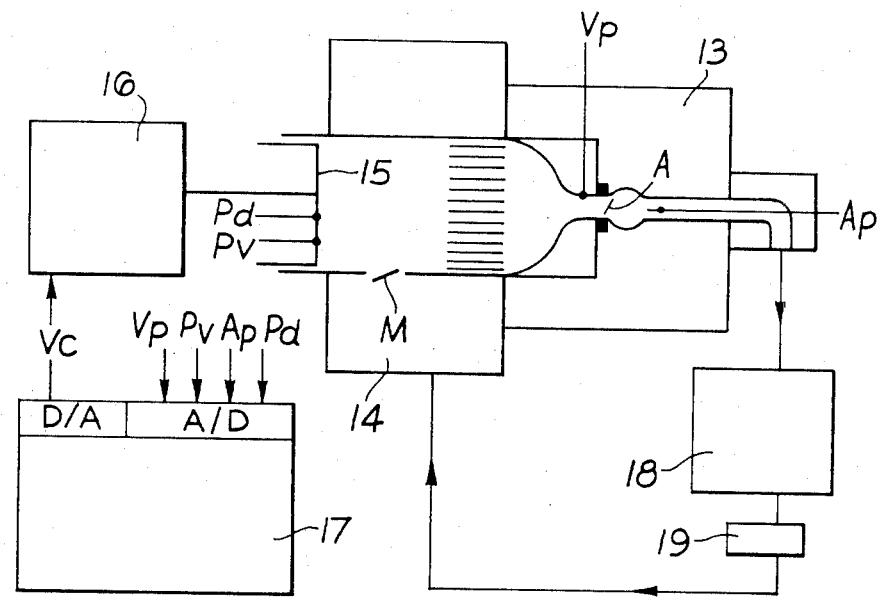

FIGS. 3(a) and (b) are side elevations at 90° to each other of the frame of the valve replacement of FIGS. 1 and 2;

FIG. 3(c) is an underneath view of FIG. 3(a);

FIG. 3(d) corresponds to FIG. 3(c) but shows how the base can deform to a D-shape;

FIG. 4 is a diagram illustrating how the shape of each leaflet of the valve of FIGS. 1 and 2 is derived;

FIG. 5 corresponds to FIG. 3(a) but shows the frame of a bicuspid mitral valve replacement with the posts displaced from the ends of the diameter of the base towards the portion of lesser flexibility;

FIG. 6 is a perspective view of a tricuspid mitral valve replacement in accordance with the invention;

FIG. 7 is an underneath view or inflow aspect of the valve replacement of FIG. 6;

FIG. 8 is a diagram of a test rig for testing valves; and

FIG. 9 is a comparative table of test results.

In FIGS. 1 to 3, a bioprosthetic bicuspid mitral valve replacement comprises a flexible plastics frame 1 (FIG. 3) having a ring-shaped base 2 and a pair of upstanding posts 3 at opposite ends of a diameter and dividing the base into two portions 2A, 2B of varying flexibility, together with two animal tissue leaflets 4 (FIGS. 1 and 2) each having a periphery consisting of a free portion 4A extending between the tips 3X of the posts 3 and a fixed portion 4B secured and sealed to corresponding sides of the posts and the adjacent portion of the base.

The flexible frame 1 is formed of polyformaldehyde, such as Delrin polymer sold by Dupont covered with polyethylene terephthalate, such as Dacron cloth 5 (FIG. 1), with the differential flexibility afforded by differing thicknesses of Delrin in the respective portions 2A, 2B of the base 2 into which the posts 3 merge at each side by way of a continuous curve 6 from the rounded tip 3X of one post 3 to the rounded tip 3X of the other post 3.

FIGS. 1 and 2 show the leaflets 4 in their natural positions after attachment to the cloth-covered frame 1, which is shown stitched to a sewing ring 7 through which it can be attached to the circumference of the auriculo-ventricular orifice in a heart (not shown), with the portion 2B of the base 2 of greater flexibility adjacent the aortic valve, whereby the base can deform to an approximate D-shape (as shown by FIG. 3) as is the case with the natural mitral valve.

The valve leaflets 4 are cut from a flat sheet of fully fixed (i.e. gluteraldehyde treated) animal tissue (e.g., bovine or calf pericardium) in the manner shown in FIG. 4 in which the shape of each leaflet 4 corresponds to a portion of the surface of a cone 8 which portion is defined by the intersections on the conical surface of two parallel flat planes 9, 10 having peripheries on the conical surface corresponding in length respectively to the circumference of the ring-shaped base 2 and the distance between the tips 3X of the posts 3 of the frame 1, and a third intersection on the conical surface of a curved plane 11 concave towards the apex 12 of the cone 8 and intersecting the two parallel flat planes 9, 10 at opposite sides of the cone, the spacing of the flat planes and the curvature of the curved plane (which changes throughout its length) being such that the development 4B of the curved plane 11 on the conical surface matches in length and curvature the continuously blending curve 6 of one arcuate portion 2A or 2B of the ring-shaped base 2 and the adjacent sides of the posts 3, so that no moulding or stress-fixing of the leaflet 4 is required. References D,d and H,h in FIGS. 3 and 4 indicate corresponding diameters and heights respectively.

In FIGS. 3(a) and 3(b) the broken lines 4A' and 4A" represent respectively the open positions and closed (or coaptation) positions of the free edges 4A of the leaflets 4.

As previously mentioned, and as will be seen in FIG. 3 the posts 3 are disposed at opposite ends of a diameter of the undistorted base 2; on the other hand, FIG. 5 shows the posts 3 displaced towards the portion 2A of lesser flexibility to accommodate leaflets 4X, 4Y of unequal size, as in the natural mitral valve, in which case the leaflets are cut from flat sheet as in FIG. 4 but with different cone angles appropriate to the respective leaflets.

In FIGS. 6 and 7 a bioprosthetic tricuspid mitral valve replacement comprises a flexible plastics frame 1 having a ring-shaped base 2 and three upstanding posts 3 disposed at regular intervals round the undistorted base, which has two portions 2A, 2B of varying flexibility, afforded by a greater thickness in the portion 2A than in the portion 2B, which latter is therefore more flexible, whereby the base can deform in the manner described with reference to FIG. 3(d). Three animal tissue leaflets 4 each having periphery consist of a free portion 4A extending between the tips 3X of posts and a fixed portion 4B secured (after covering the frame 1 with cloth 5) and sealed to corresponding sides of the posts 3 and adjacent portion of the base 2. The tricuspid valve replacement is shown with its leaflets 4 in their natural positions after attachment to the cloth covered frame 1, which is shown stitched to a sewing ring 7 through which it can be attached to the circumference of the auriculo-ventricular orifice in a heart (not shown), thereafter to function in similar manner to the bicuspid valve replacement of FIGS. 1 to 3. The three leaflets 4 of the tricuspid valve replacement are each cut from flat sheet as in FIG. 4 but with different cone angle and diameters appropriate to the different lengths 4A and 4B.

In FIG. 8, M and A represent test valves in the mitral and aortic positions respectively within a sealed test chamber 13 having an inlet fluid reservoir 14. Pumping is effected by a piston 15 with a velocity servo system 16 coupled to the digital/analogue (D/A) unit of a microcomputer 17, the flow being in the direction of the arrows from the aortic valve A to the mitral valve M via a lumped parameter model of afterload 18 and a turbine flowmeter 19. Vp and Ap are model ventricular and aortic pressures respectively monitored with purpose built catheter tipped devices, Pd and Pv are the displacement and velocity respectively of the piston at any instant, and Vc is the piston control signal derived from the microcomputer 17 through its digital-/analogue (D/A) unit.

A bicuspid mitral valve replacement in accordance with FIGS. 1 and 2 and two currently used tricuspid mitral valve replacements of corresponding size were tested for pressure drop and regurgitation in the mitral position M. A summary of the test results is given in the table of FIG. 9 and shows that the performance of the new bicuspid valve replacement compares very favourably with the two currently available bioprosthetic tricuspid mitral valve replacements. In particular the comparison with the Ionescu-Shiley valve indicates similar pressure drops with appreciably less regurgitation.

What we claim is:

1. A bioprosthetic mitral valve replacement comprising a frame having a ring-shaped base and at least a pair of upstanding posts merging into the base by way of a continuous curve from the tip of one post to the tip of the other post, valve leaflets each having a free portion extending between the tips of the posts and a fixed portion secured and sealed to corresponding sides of the posts and the adjacent portion of the base, the valve leaflets being cut from a flat sheet of fully fixed animal tissue and the shape of each leaflet corresponding to a portion of a surface of a cone which portion is defined by the intersections on the conical surface of two parallel flat planes having peripheries on the conical surface corresponding in length respectively to the circumference of the ring-shaped base and the distance between the tips of the posts of the frame, and a third intersection on the conical surface of a curved plane concave towards the apex of the cone and intersecting the two parallel flat planes at opposite sides of the cone, the spacing of the flat planes and the curvature of the curved plane being such that the development of the curved plane on the conical surface matches in length and curvature the continuously blending curve of one arcuate portion of the ring-shaped base and the adjacent sides of the posts.

2. A mitral valve replacement as in claim 1, wherein the base is flexible and a pair of upstanding posts divide the base into two portions of differing flexibility, with lesser flexibility at one side between the posts than at the other side between the posts.

3. A mitral valve replacement as in claim 2, wherein the posts are disposed at opposite ends of a diameter of the undistorted base.

4. A mitral valve replacement as in claim 2, wherein the posts are displaced from the opposite ends of a diameter of the undistorted base towards the portion of lesser flexibility, and the leaflets are of correspondingly equal size.

5. A mitral valve replacement as in claim 1, wherein three posts are disposed at regular intervals round the base.

6. A mitral valve replacement as in claim 1, wherein the frame is formed of polyformaldehyde covered with polyethylene terephthalate cloth.

7. A mitral valve replacement as in claim 2, wherein the differential flexibility is afforded by providing differing thicknesses of polyformaldehyde to either side of the posts.

* * * * *